(12) United States Patent
Lindquist et al.

(10) Patent No.: US 7,887,830 B2
(45) Date of Patent: Feb. 15, 2011

(54) MEDICAL DEVICES HAVING POLYMERIC REGIONS BASED ON STYRENE-ISOBUTYLENE COPOLYMERS

(75) Inventors: Jeffrey S. Lindquist, Maple Grove, MN (US); Frederick H. Strickler, Natick, MA (US); Mark Boden, Harrisville, RI (US); Jan Seppala, Greenfield, MN (US); Paul J. Miller, Vadnais Heights, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 133 days.

(21) Appl. No.: 12/070,806

(22) Filed: Feb. 21, 2008

(65) Prior Publication Data

US 2008/0206304 A1 Aug. 28, 2008

Related U.S. Application Data

(60) Provisional application No. 60/903,589, filed on Feb. 27, 2007.

(51) Int. Cl.
*A61F 2/00* (2006.01)
(52) U.S. Cl. .................. 424/423; 623/1.1; 526/329.2; 526/348.7
(58) Field of Classification Search ........................ None
See application file for complete search history.

(56) References Cited

U.S. PATENT DOCUMENTS

| | | | |
|---|---|---|---|
| 5,741,331 A * | 4/1998 | Pinchuk ........................ | 424/423 |
| 6,545,097 B2 * | 4/2003 | Pinchuk et al. ............. | 525/240 |
| 2002/0107330 A1 | 8/2002 | Pinchuk et al. | |
| 2005/0125003 A1 | 6/2005 | Pinchuk et al. | |
| 2005/0208107 A1 * | 9/2005 | Helmus et al. .............. | 424/443 |
| 2006/0013867 A1 | 1/2006 | Richard et al. | |
| 2006/0178733 A1 | 8/2006 | Pinchuk et al. | |
| 2006/0257355 A1 * | 11/2006 | Stewart et al. ........... | 424/78.27 |
| 2007/0118210 A1 * | 5/2007 | Pinchuk ...................... | 623/1.26 |

FOREIGN PATENT DOCUMENTS

| | | |
|---|---|---|
| WO | 0247731 A2 | 6/2002 |
| WO | 20060065837 A2 | 6/2006 |
| WO | 2007062320 A2 | 5/2007 |
| WO | 2008027107 A2 | 3/2008 |

OTHER PUBLICATIONS

Shrirang V. Ranade et al., "Styrenic block copolymers for biomaterial and drug delivery applications", *Acta Biomater.*, Jan. 2005, 1(1), pp. 137-144.
Virmani Renu et al., "Localized Hypersensitivity and Late Coronary Thrombosis Secondary to a Sirolimus-Eluting Stent Should We Be Cautious?", *Circulation* Feb. 17, 2004, 109(6) 701-5.
Miklos Gyor et al., "Living Carbocationic Polymerization of Isobutylene with Blocked Bifunctional Initiators in the Presence of Di-*tert*-Butylpyridine as a Proton Trap", *J. of Macromolecular Sci., Pure and Applied Chem.*, 1992, A29(8), pp. 639-653.
Dawn M.Crawford et al. "Structure/Property Relationships in Polystyrene-Polyisobutylene-Polystyrene Block Copolymers," *Thermica Acta*, 367-368, 2001, pp. 125-134.
P. Antony et al. "Investigation of the Rheological and Mechanical Properties of a Novel Polystyrene-Polyisobutylene-Polystyrene Triblock Copolymer and Its Blends with Polystyrene", *Polym. Eng. Sci.*, 43 (1), 2003, pp. 243-253.
J.E Puskas, et al., "The effect of hard and soft segment composition and molecular architecture on the morphology and mechanical properties of polystyrene-polyisobutylene thermoplastic elastomeric block copolymers", *European Polymer Journal*, 39, 2003, pp. 2041-2049.
Shrirang V. Ranade et al.,"Physical characterization of controlled release of paclitaxel from the TAXUS Express2 drug-eluting stent," *J Biomed Mater* Res A. Dec. 15, 2004, 71(4), pp. 625-634.
S. Brody et al., "Characterization Nanoscale Topography of the Aortic Heart Valve Basement Membrane for Tissue Engineering Heart Valve Scaffold Design", Tissue Engineering, vol. 12, Nov. 2, 2006, pp. 413-421.

\* cited by examiner

*Primary Examiner*—Robert A Wax
*Assistant Examiner*—Bethany Barham
(74) *Attorney, Agent, or Firm*—Mayer & William; David B. Bonham; Keum J. Park

(57) ABSTRACT

According to an aspect of the present invention, implantable or insertable medical devices are provided, which contain one or more polymeric regions. These polymeric regions, in turn, contain one or more polymers, at least one of which is a copolymer that includes a styrene monomer and an isobutylene monomer. Moreover, the styrene monomer content of the copolymer typically ranges from 25 to 50 mol %.

17 Claims, 2 Drawing Sheets

US 7,887,830 B2

MEDICAL DEVICES HAVING POLYMERIC REGIONS BASED ON STYRENE-ISOBUTYLENE COPOLYMERS

STATEMENT OF RELATED APPLICATION

This application claims the benefit of U.S. Provisional Patent Application Ser. No. 60/903,589, filed Feb. 27, 2007, entitled "Medical Devices Having Polymeric Regions Based on Styrene-Isobutylene Copolymers", which is incorporated by reference herein in its entirety.

FIELD OF THE INVENTION

The present invention relates generally to medical devices, and more particularly to implantable or insertable medical devices which contain polymeric regions.

BACKGROUND OF THE INVENTION

Materials which are suitable for use in making implantable or insertable medical devices typically exhibit one or more of the qualities of biocompatibility, extrudability, moldability, fiber forming properties, tensile strength, elasticity, durability, and the like. Moreover, in medical devices from which a therapeutic agent is released, suitable materials for use will typically exhibit a release profile appropriate for the disease or condition being treated. For example, numerous polymer-based medical devices have been developed for the delivery of therapeutic agents to the body. Examples include drug eluting coronary stents, which are commercially available from Boston Scientific Corp. (TAXUS), Johnson & Johnson (CYPHER), and others. See S. V. Ranade et al., *Acta Biomater.* 2005 Jan.; 1(1): 137-44 and R. Virmani et al., *Circulation* 2004 Feb. 17, 109(6) 701-5.

SUMMARY OF THE INVENTION

According to an aspect of the present invention, implantable or insertable medical devices are provided, which contain one or more polymeric regions, which may correspond, for example, to an entire medical device or to one or more portions of a medical device (e.g., a coating, etc.). These polymeric regions, in turn, contain one or more polymers, at least one of which is a copolymer that includes styrene and isobutylene. Moreover, the styrene content of the copolymer typically ranges from 17 to 50 mol %.

An advantage of the invention is that materials may be provided for medical devices which display reduced tack and reduced webbing, relative to copolymers having lower styrene contents.

Another advantage of the invention is that materials may be provided for medical devices which display reduced tack and reduced webbing, relative to copolymers having lower styrene contents and which have a reduced tendency to undergo permanent deformation in use, relative to copolymers having higher styrene contents.

Further advantages include tailorable properties over a broad range of compositions. Medical devices that require reduced tack, friction and webbing, while also maintaining elasticity, can be obtained using higher styrene contents. Medical devices that require enhanced flexibility can be obtained using lower styrene contents. A particularly preferred range is 25-40 mol % styrene.

These and other aspects, embodiments and advantages of the present invention will become immediately apparent to those of ordinary skill in the art upon review of the Detailed Description and Claims to follow.

DETAILED DESCRIPTION OF THE INVENTION

Figure 1:
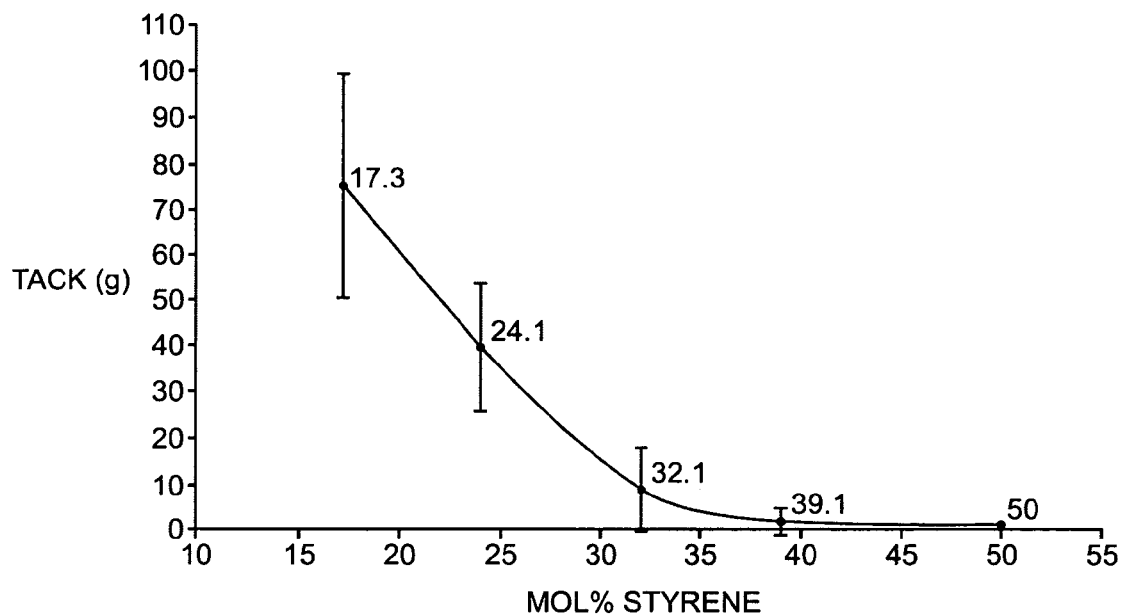
FIG. 1 is a plot of surface tack vs. % styrene for various SIBS compositions vis-à-vis a stainless steel sample.

As noted above, in one aspect, the present invention provides implantable or insertable medical devices, which contain one or more polymeric regions. These polymeric regions, in turn, contain one or more polymers, at least one of which is a copolymer that includes a styrene monomer and an isobutylene monomer. Moreover, the styrene monomer content of the copolymer typically ranges from 17 to 50 mol % (i.e., 17 mol % to 18 mol % to 19 mol % to 20 mol % to 21 mol % to 22 mol % to 23 mol % to 24 mol % to 25 mol % to 26 mol % to 27 mol % to 28 mol % to 29 mol % to 30 mol % to 31 mol % to 32 mol % to 33 mol % to 34 mol % to 35 mol % to 36 mol % to 37 mol % to 38 mol % to 39 mol % to 40 mol % to 42 mol % to 45 mol % to 50 mol %), with 25 to 40 mol % being more typical in certain applications, such as stent coatings.

As used herein a "polymeric region" is a region that contains one or more types of polymers, and typically contains at least 50 wt % polymers, at least 75 wt % polymers, or even more.

As used herein, "polymers" are molecules containing multiple copies (e.g., 5 to 10 to 25 to 50 to 100 to 250 to 500 to 1000 or more copies) of one or more constitutional units, commonly referred to as monomers. As used herein, the term "monomers" may refer to the free monomers and those that are incorporated into polymers, with the distinction being clear from the context in which the term is used. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating), and block copolymers. As used herein, "block copolymers" are copolymers that contain two or more differing polymer blocks, for instance, because a constitutional unit (i.e., a monomer) is found in one polymer block that is not found in another polymer block. As used herein, a "polymer block" is a grouping of constitutional units (e.g., 5 to 10 to 25 to 50 to 100 to 250 to 500 to 1000 or more units). In certain embodiments, the polymer blocks contain more than 10,000 constitutional units. For example, the SIBS copolymers described in the Examples below contain about 80,000 isobutylene repeating units and about 30,000 to 50,000 polystyrene repeating units.

Blocks can be branched or unbranched. Blocks can contain a single type of constitutional unit ("homopolymeric blocks") or multiple types of constitutional units ("copolymeric blocks") which may be provided, for example, in a random, statistical, gradient, or periodic (e.g., alternating) distribution.

Examples of such structures include (a) block copolymers having alternating blocks of the type $(SI)_m$, $I(SI)_m$ and $S(IS)_m$ where S is a poly(styrene) block, I is a poly(isobutylene) block, m is a positive whole number of 1 or more, and (b) block copolymers having multi-arm geometries, such as $X(IS)_n$, and $X(SI)_n$, where n is a positive whole number of 2 or more and X is a hub species (e.g., an initiator molecule residue, a residue of a molecule to which preformed polymer chains are attached, etc.). In addition to the hub species mentioned above, copolymers such as those above can contain a variety of other non-polymer-chain species, which are commonly present in copolymers, including capping molecules, and linking residues. Note that non-polymer species, such as hub species, linking species, etc. are generally ignored in describing block copolymer morphology, for example, with $X(IS)_2$ being designated as an SIS triblock copolymer. Other examples of block copolymers include comb copolymers having an I chain backbone and multiple S side chains, as well as comb copolymers having an S chain backbone and multiple I side chains.

Copolymers in accordance with the present invention may be produced by living cationic polymerization as described in M. Gyor et al., *J. of Macromolecular Sci., Pure and Applied Chem.*, 1992, A29(8), 639 and in U.S. Pat. App. No. 2002/0107330 to Pinchuk et al.

Medical devices benefiting from the present invention include a variety of implantable or insertable medical devices, which are implanted or inserted into a subject, either for procedural uses or as implants. Examples include stents (including coronary artery stents, peripheral vascular stents such as cerebral stents, urethral stents, ureteral stents, biliary stents, tracheal stents, gastrointestinal stents and esophageal stents), stent grafts, vascular grafts, catheters (e.g., renal or vascular catheters such as balloon catheters), guide wires, balloons, filters (e.g., vena cava filters), vascular access ports, embolization devices including cerebral aneurysm filler coils (including Guglilmi detachable coils and metal coils), myocardial plugs, pacemaker leads, left ventricular assist hearts and pumps, total artificial hearts, heart valves, vascular valves, cochlear implants, tissue bulking devices, tissue engineering scaffolds for cartilage, bone, skin and other in vivo tissue regeneration, sutures, suture anchors, anastomosis clips and rings, tissue staples and ligating clips at surgical sites, cannulae, metal wire ligatures, joint prostheses, as well as various other medical devices that are adapted for implantation or insertion into the body.

The medical devices of the present invention include implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

In some embodiments, the polymeric regions of the present invention correspond to an entire medical device. In other embodiments, the polymeric regions correspond or to one or more portions of a medical device. For instance, the polymeric regions can be in the form of one or more medical device components, in the form of one or more fibers which are incorporated into a medical device, in the form of one or more polymeric layers formed over all or only a portion of an underlying medical device substrate, and so forth. Layers can be provided over an underlying substrate at a variety of locations, and in a variety of shapes (e.g., in desired patterns, for instance, using appropriate application or masking techniques), and they can be of different compositions. As used herein a "layer" of a given material is a region of that material whose thickness is small compared to both its length and width. As used herein a layer need not be planar, for example, taking on the contours of an underlying substrate. Layers can be discontinuous (e.g., patterned). Terms such as "film," "layer" and "coating" may be used interchangeably herein.

Materials for use as underlying substrates include polymeric materials, ceramic materials and metallic materials such as stainless steel or nitinol.

In some aspects, the polymeric regions of the present invention control the release of one or more therapeutic agents, in which case the therapeutic agent may be disposed, for example, beneath and/or within the polymeric region. Such "polymeric release regions" include carrier regions and barrier regions. By "carrier region" is meant a polymeric release region which further comprises a therapeutic agent and from which the therapeutic agent is released. For example, in some embodiments, the carrier region constitutes the entirety of the medical device (e.g., provided in the form of a stent body). In other embodiments, the carrier region corresponds to only a portion of the device (e.g., a coating overlying a medical device substrate such as a stent body). By "barrier region" is meant a region which is disposed between a source of therapeutic agent and a site of intended release, and which controls the rate at which therapeutic agent is released. For example, in some embodiments, the medical device consists of a barrier region that surrounds a source of therapeutic agent. In other embodiments, the barrier region is disposed over a source of therapeutic agent, which is in turn disposed over all or a portion of a medical device substrate.

In addition to the attributes of the polymer or polymers making up the polymeric release regions, the therapeutic agent release profile is affected by other factors such as the size, number and/or position of the polymeric release regions within the device. For example, the release profile of polymeric carrier and barrier layers in accordance with the presenting invention can be modified by varying the thickness and/or surface areas of the same. Moreover, multiple polymeric regions can be employed to modify the release profile. For example, multiple carrier or barrier layers, either having the same or different content (e.g., different polymeric and/or therapeutic agent content), can be stacked on top of one another (hence, carrier layers can act as barrier layers in some embodiments), can be positioned laterally with respect to one another, and so forth.

As a specific example, for tubular devices such as stents (which can comprise, for example, a laser or mechanically cut tube, one or more braided, woven, or knitted filaments, etc.), polymeric release layers can be provided on the luminal surfaces, on the abluminal surfaces, on the lateral surfaces between the luminal and abluminal surfaces (including the ends), patterned along the luminal or abluminal length of the devices, and so forth. Moreover, release layers can control the release of the same or different therapeutic agents. It is therefore possible, for example, to release different therapeutic agents from different locations on the medical device. For instance, it is possible to provide a tubular medical device (e.g., a vascular stent) having a first release layer which contains or is disposed over a first biologically active agent (e.g., an antithrombotic agent) at its inner, luminal surface and a second release layer which contains or is disposed over a second biologically active agent that differs from the first biologically active agent (e.g., an antiproliferative agent) at its outer, abluminal surface (as well as on the ends, if desired).

In addition to the above copolymers, the polymeric regions for use in conjunction with the present invention also optionally contain supplemental polymers. Examples of supplemental polymers can be selected, for example, from those listed in U.S. Pat. Pub. No. 2006/0013867 to Richard et al., among many others. The supplemental polymers may be provided for various reasons. Supplemental polymers may be introduced, for example, to render the polymeric regions more hydrophilic, to modulate the release profile of a therapeutic agent, if any, among other reasons.

As noted above, the medical devices of the present invention also optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary non-genetic therapeutic agents for use in conjunction with the present invention include: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include taxanes such as paclitaxel, (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methylprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Further additional therapeutic agents useful for the practice of the present invention are also disclosed in U.S. Pat. No. 5,733,925 assigned to NeoRx Corporation, the entire disclosure of which is incorporated by reference.

Where a therapeutic agent is included, a wide range of therapeutic agent loadings can be used in conjunction with the medical devices of the present invention, with the therapeutically effective amount being readily determined by those of ordinary skill in the art and ultimately depending, for example, upon the condition to be treated, the age, sex and condition of the subject, the nature of the therapeutic agent, the nature of the polymeric region(s), and the nature of the medical device, among other factors.

Numerous techniques are available for forming polymeric regions in accordance with the present invention.

For example, in some embodiments, thermoplastic processing techniques are used to form the polymeric regions of the present invention. Using these techniques, polymeric regions can be formed by first providing a melt that contains the polymer(s) that form the polymeric region, among other optional additives, if desired, and subsequently cooling the melt. Examples of thermoplastic techniques include compression molding, injection molding, blow molding, spinning, vacuum forming and calendaring, as well as extrusion into sheets, fibers, rods, tubes and other cross-sectional profiles of various lengths. Using these and other thermoplastic processing techniques, a variety of polymeric regions can be formed In other embodiments, solvent-based techniques are used to form the polymeric regions of the present invention. Using these techniques, polymeric regions can be formed by first providing a solution that contains the polymer(s) that form the polymeric region, among other optional additives, if desired, and subsequently removing the solvent. The solvent that is ultimately selected will contain one or more solvent species, which are generally selected based on their ability to dissolve the polymer(s) and optional additives that make up the polymeric region, as well as other factors, including drying rate, surface tension, etc. Examples of solvent-based techniques include solvent casting techniques, spin coating techniques, web coating techniques, solvent spraying techniques, dipping techniques, techniques involving coating via mechanical suspension including air suspension, ink jet techniques, electrostatic techniques, and combinations of these processes, among others.

In some embodiments of the invention, a polymer containing solution (where solvent-based processing is employed) or polymer melt (where thermoplastic processing is employed) is applied to a substrate to form a polymeric region. For example, the substrate can correspond to all or a portion of an implantable or insertable medical device to which a polymeric region is applied. The substrate can also be, for example, a template, such as a mold, from which the polymeric region is removed after solidification. In other embodiments, for example, fiber spinning, extrusion and co-extrusion techniques, one or more polymeric regions are formed without the aid of a substrate.

If it is desired to provide one or more therapeutic agents (and/or any other optional additives) within the polymeric region, so long as these agents are stable under processing conditions, then they may be provided within the polymer containing solution or polymer melt and co-processed along with the polymer(s).

Alternatively, therapeutic and/or other optional additives may be introduced subsequent to the formation of the polymeric region in some embodiments. For instance, in some embodiments, the therapeutic and/or other optional agents are dissolved or dispersed within a solvent, and the resulting solution contacted (e.g., using one or more of the application techniques described above, such as dipping, spraying, etc.) with a previously formed polymeric region.

As noted above, barrier regions are provided over therapeutic-agent-containing regions in some embodiments of the invention. In these embodiments, a polymeric barrier region can be formed over a therapeutic-agent-containing region, for example, using one of the solvent based or thermoplastic techniques described above. Alternatively, a previously formed polymeric region can be adhered over a therapeutic agent containing region.

EXAMPLE 1

Preparation of SIBS Copolymer Compositions

Five samples of poly(styrene-b-isobutylene-b-styrene) triblock copolymer (SIBS) were prepared using known techniques. See, e.g., M. Gyor et al., *J. of Macromolecular Sci., Pure and Applied Chem.*, 1992, A29(8), 639 and in U.S. Pat. App. No. 2002/0107330 to Pinchuk et al.

The number average molecular weight, the polyisobutylene polydispersity index (prior to polystyrene block synthesis), and the overall triblock copolymer polydispersity index were measured for each and presented in Table. 1.

TABLE 1

| Mol % Styrene | SIBS Mol. Wt., Mn | SIBS PDI | PIB PDI |
|---|---|---|---|
| 17.3% | 105,969 | 1.40 | 1.10 |
| 24.1% | 126,179 | 1.58 | 1.13 |
| 31.6% | 97,834 | 1.7 | 1.12 |
| 39.1% | 88,201 | 1.9 | 1.19 |
| 50.8% | 94,752 | 2.0 | 1.16 |

EXAMPLE 2

Solvent-Based Coating

A solution was formed for each of the above SIBS samples. Specifically, solutions were made containing (1) 94% toluene, (2) 5%, tetrahydrofuran and (3) 1% SIBS. The solution of interest was then placed in a syringe pump and fed to a spray nozzle. Stents, specifically, Express® SD, SV and WH stainless steel stents and Liberté™ WH stainless steel stents (Boston Scientific Inc., Natick Mass., USA), were coated as follows: The stent was first mounted onto a holding device an rotated (e.g., at 45 RPM) during spraying to ensure uniform coverage. For instance, a nozzle pressurized for a flow rate of 6.3 mL/hr may be provided at a distance of 1.0 inch from the stent and moved back and for longitudinally relative to the rotating stent at between 0.3-0.5 mm/sec to produce a coating having a thickness of 20 microns. The stent was then dried by placing it in a preheated oven (e.g., for 30 minutes at 65° C., followed by 3 hours at 70° C.).

EXAMPLE 3

Stent Testing

Coated stents prepared according to Example 2 were nominally expanded to their anticipated expansion diameter and also over-expanded using a balloon of suitable diameter.

SEM (Scanning Electron Microscopy) was utilized to evaluate topological and coating integrity inconsistencies. Specifically, each sample was mounted on an aluminum stub and lightly gold coated (about 200 angstroms coating thickness). Magnifications of 75 to 2000× were used to obtain images.

FESEM (Field Emission Scanning Electron Microscopy) was utilized to further evaluate areas of interest which were identified during initial SEM analysis (with no depth of measurement) and utilized a JEOL 6300F, Oxford INCA-300 EDS (Energy Dispersive Spectrometer), 5 kV accelerated voltage, instrument. Each sample was mounted on an aluminum stub and platinum coated (about 200 angstroms coating thickness). Representative comparative images were generated for each stent. Magnifications to 50,000× and various image tilt angles were utilized to obtain images sizes ranging from approximately 700 micrometers to 20 micrometers.

SEM investigation after nominal stent expansion indicated that the coatings of the lower styrene content (i.e., 17.3, 24.1, 31.6 and 39.1 mol %) SIBS samples were virtually free of defects, with no evidence of micro-deformations or cracking. The higher styrene content (50.8 mol %) coated stent samples, possessed micro-deformations (crazing), in many of the higher strain areas of all stent samples tested.

Upon over-expansion, investigation utilizing SEM and FESEM indicated that the 17.3, 24.1, and 31.6 mol % styrene SIBS samples were virtually free of defects, with no evidence of coating micro-deformations or cracking, whereas the 39.1 and 50.8 mol % styrene SIBS samples displayed micro deformations (crazing) in many of the higher strain areas of all stent samples evaluated. Analysis of a small sample set of representative micro-formations, via EDS, indicated that the micro-deformations did not expose the metal stent substrate for the 39.1 mol % styrene SIBS samples. Moreover, most of the over-expanded stents coated with 50.8 mol % styrene SIBS displayed visual evidence of actual coating cracks, or tears, wherein the metal stent substrate was exposed (confirmed via EDS utilizing FESEM). The micro-deformations observed for the 50.8 mol % styrene SIBS coating were larger in size and more common in occurrence (observed on nearly every strut hinge area) than those of observed for the 39.1 mol % styrene SIBS coating.

Figure 2:
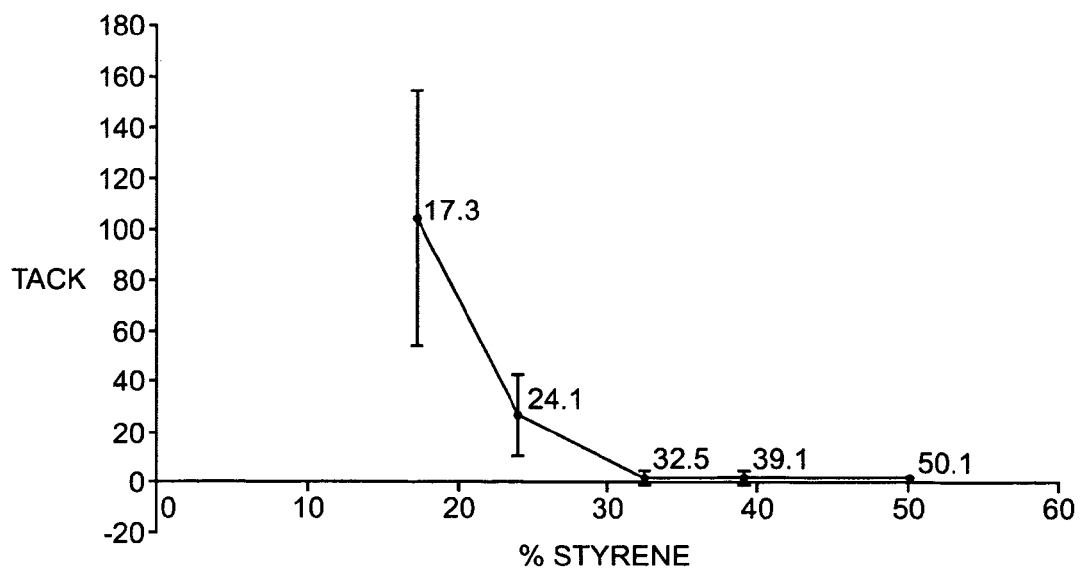
FIG. 2 is a plot of surface tack vs. % styrene for various SIBS compositions vis-à-vis a poly(ether-block-amide) copolymer sample.

Surface tack was also evaluated for each of the samples using a technique in which a stainless steel probe, approaching the coated stent at an established rate, is brought into contact with the coated stent surface for an established period of time, and is then withdrawn at an established rate utilizing a motor driven device. The peak force required to remove the probe from the coated stent probe surface was indicative of the surface tack of the stent. The results are presented in FIG. 1. Analogous testing was performed using Atofina Pebax® 7233 grade polyether-block-polyamide. The results are presented in FIG. 2.

Analysis of the data gathered indicated that the tack properties of the SIBS is inversely related to polystyrene content of the same, with less tack being more desirable for applications where lower tack results in improved delivery performance. In particular, a drop in tack of nearly 100% was observed when one went from the 17.3 mol % styrene SIBS to the 31.6 mol % styrene SIBS. The tack properties of the 31.6, 39.1 and 50.8 mol % styrene SIBS compositions were observed to be very low.

Figure 3:
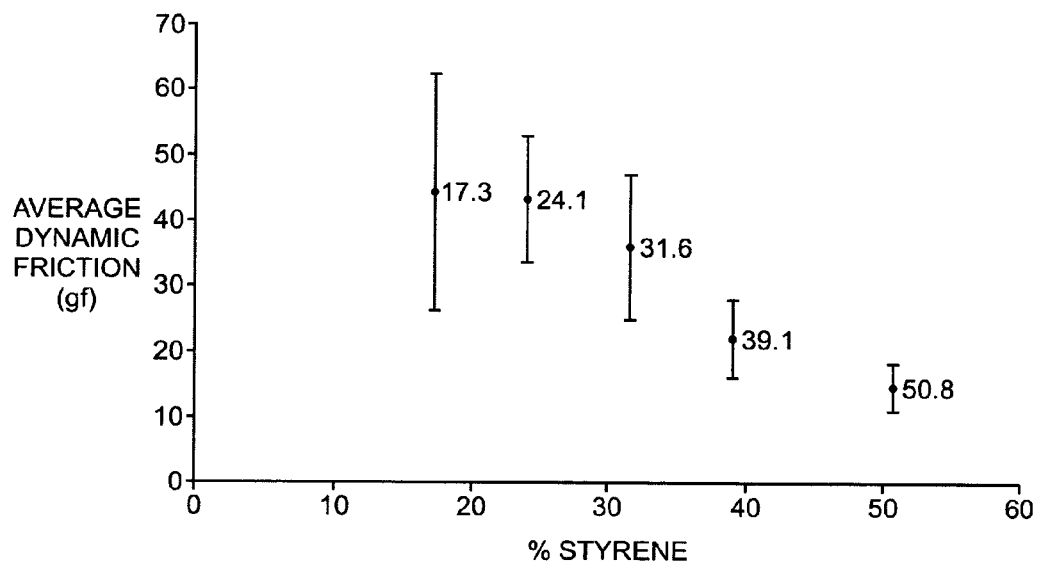
FIG. 3 is a plot of average dynamic friction vs. % styrene for various SIBS compositions vis-à-vis a polyether-block-polyamide copolymer sample.

Surface friction properties for the various SIBS compositions (coated on Liberté™ BE stents) were evaluated utilizing a benchtop mechanical testing system (MTS, Bionix 100) to determining differences in the relative static and kinetic coefficients of friction (relative to an Atofina Pebax®7233 grade polyether-block-polyamide coated mandrel) between the samples. Results are presented in FIG. 3. As with tack, static and kinetic friction analysis indicated that friction properties were inversely related to the polystyrene content of the copolymer, although the differences were not as dramatic.

Figure 4:
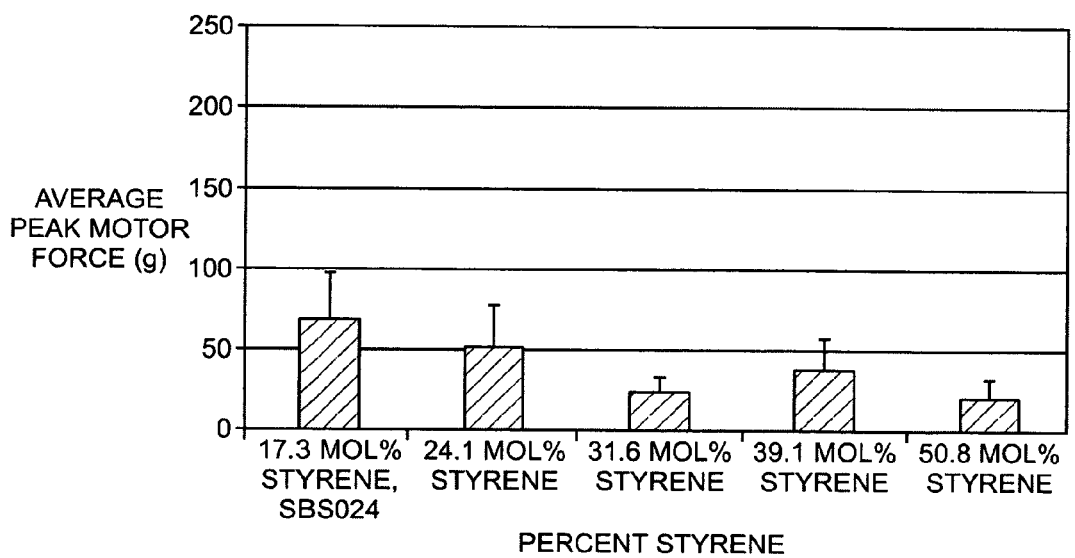
FIG. 4 is a plot of average peak motor force required to withdraw a balloon catheter from coated stents (deployed with a simulated curved artery) vs. % styrene for various SIBS compositions.

The average peak force required to withdraw a Pebax® balloon catheter from coated Liberté™ stents deployed with a simulated curved artery were also measured and presented in FIG. 4. A reduction in withdrawal force was observed in going from 17 to 32 mol % styrene in the SIBS coatings.

Fatigue properties were evaluated utilizing an EnduraTec Pulsatile Fatigue Tester (4 tube system) with integrated computer. The tester creates distention pulses in latex tubing within which a coated stent (i.e., Express® SD) was deployed. After 10 million cycles, fatigue failure examination was conducted both optically at 80x magnification and utilizing SEM from 50 to 5,000x magnification. Analysis of the 17.3-39.1 mol % styrene SIBS compositions did not show any indication of fatigue-related coating failure. The 50.8 mol % styrene SIBS composition showed evidence of craze deformation, which did not expose the stent metal substrate.

Occurrences of webbing between stent struts were seen to be inversely related to styrene content. Upon stent over-expansion, no coat webbing was observed upon visual and SEM inspection for stents coated with the 50.8, 39.1, and 31.6 mol % styrene SIBS compositions. Webbing was noted, however, for stents coated with the 24.1 and 17.3 mol % styrene SIBS, with more observations of webbing being noted for the stents coated with the 17.3 mol % styrene SIBS than with the 24.1 mol % styrene SIBS.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising a polymeric region, wherein said polymeric region is a coating disposed over a medical device substrate, said polymeric region comprising a copolymer that comprises a styrene monomer and an isobutylene monomer, wherein the styrene monomer content of the copolymer ranges from 30 to 40 mol %.

2. The medical device of claim 1, wherein said copolymer is a block copolymer that comprises a polystyrene block and a polyisobutylene block.

3. The medical device of claim 2, wherein the styrene monomer content of the copolymer ranges from 30 to 35 mol %.

4. The medical device of claim 2, wherein the styrene monomer content of the copolymer ranges from 35 to 40 mol %.

5. The medical device of claim 2, wherein said block copolymer is a branched copolymer.

6. The medical device of claim 2, wherein said block copolymer is a linear copolymer.

7. The medical device of claim 2, wherein the block copolymer is a triblock copolymer comprising a polyisobutylene central block and two polystyrene end blocks.

8. The medical device of claim 2, wherein said polymeric region comprises at least 75 wt % of said block copolymer.

9. The medical device of claim 2, wherein said medical device further comprises a therapeutic agent.

10. The medical device of claim 9, wherein said therapeutic agent is disposed within said polymeric region.

11. The medical device of claim 9, wherein said therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

12. The medical device of claim 2, wherein said polymeric region further comprises a supplemental polymer in addition to said block copolymer.

13. The medical device of claim 2, wherein said medical device is selected from a guide wire, a balloon, a vena cava filter, a catheter, a stent, a stent graft, a vascular graft, a cerebral aneurysm filler coil, a myocardial plug, a heart valve, a vascular valve, a pacemaker lead, and a cochlear implant.

14. The medical device of claim 1, wherein said medical device substrate is a metallic stent.

15. An implantable or insertable medical device comprising a coating disposed over a metallic stent, said coating comprising a block copolymer that comprises a polystyrene block and a polyisobutylene block, wherein the styrene monomer content of the copolymer ranges from 30 to 40 mol %.

16. The medical device of claim 15, wherein the styrene monomer content of the copolymer ranges from 30 to 35 mol %.

17. The medical device of claim 15, wherein the styrene monomer content of the copolymer ranges from 35 to 40 mol %.

* * * * *